(12) United States Patent
Kamiyama

(10) Patent No.: US 6,669,953 B1
(45) Date of Patent: Dec. 30, 2003

(54) BLOCK COPOLYMER

(75) Inventor: Fumio Kamiyama, Kyoto (JP)

(73) Assignee: Strakan Limited (BM)

(*) Notice: Subject to any disclaimer, the term of this patent is extended or adjusted under 35 U.S.C. 154(b) by 0 days.

(21) Appl. No.: 09/462,691

(22) PCT Filed: Jul. 10, 1998

(86) PCT No.: PCT/GB98/02018

§ 371 (c)(1),
(2), (4) Date: May 8, 2000

(87) PCT Pub. No.: WO99/02141

PCT Pub. Date: Jan. 21, 1999

(30) Foreign Application Priority Data

Jul. 11, 1997 (GB) .............................................. 9714650

(51) Int. Cl.⁷ .......................... A61F 13/00; C08L 32/24; C08L 33/00; C08F 265/00; C09J 101/00
(52) U.S. Cl. ...................... 424/449; 424/443; 525/218; 525/221; 525/222; 525/223; 525/224; 525/225; 525/226; 525/227; 525/228; 525/229; 525/230; 525/301; 525/302; 156/326; 156/327
(58) Field of Search ................................ 424/448, 449, 424/443; 525/282, 267, 205, 218, 221–230, 302, 301; 156/326, 327

(56) References Cited

U.S. PATENT DOCUMENTS

| 4,575,539 | A | * | 3/1986 | DeCrosta et al. |
| 5,006,342 | A | * | 4/1991 | Cleary et al. ................ 424/445 |
| 5,082,663 | A | | 1/1992 | Konishi et al. |
| 5,183,856 | A | * | 2/1993 | Kitagawa et al. |
| 5,186,938 | A | * | 2/1993 | Sablotsky et al. |
| 5,573,778 | A | * | 11/1996 | Therriault et al. |
| 5,629,014 | A | * | 5/1997 | Kwiatek et al. ............. 424/449 |
| 5,958,446 | A | * | 9/1999 | Miranda et al. |
| 5,980,932 | A | * | 11/1999 | Chiang et al. ............... 424/448 |
| 6,479,073 | B1 | * | 11/2002 | Lucast et al. ................ 424/448 |

FOREIGN PATENT DOCUMENTS

| EP | 0 443 864 A1 | | 8/1991 |
| GB | 2 056 999 | * | 3/1981 |

* cited by examiner

Primary Examiner—Thurman K. Page
Assistant Examiner—Isis Ghali
(74) Attorney, Agent, or Firm—Fish & Richardson P.C.

(57) ABSTRACT

Cross-linked block copolymers are disclosed which have drug retention properties, comprising hard and soft segments, with cross-linking between the soft segments. The block copolymers can be based upon (meth)acrylic monomers, and some possess adhesive properties.

68 Claims, No Drawings

BLOCK COPOLYMER

RELATED APPLICATIONS

This application claims priority from application 9714650.0 which was filed in the United Kingdom on Jul. 11, 1997.

The present invention relates to block copolymers useful in transdermal patches as adhesives and/or drug retention means, as well as to transdermal patches comprising such block copolymers.

Transdermal patches are well known in the pharmaceutical industry and are used to deliver drugs into the skin of a patient. Drug delivery by use of a transdermal patch has a number of advantages over oral delivery methods. For example, the drug may be provided continuously over a long period, rather than in spaced apart, higher doses, and the patches are easy to apply and use.

The patch must have an adhesive portion, to allow the patch to adhere to the skin. An adhesive suitable for use in a transdermal patch should possess certain properties, including adhesion, tack and cohesion. Adhesion refers to the force with which the adhesive sticks to a surface. Tack refers to the speed at which the adhesive can form a bond with the surface, while cohesion refers to the internal strength of an adhesive and its ability to resist splitting when placed under external stress. Good cohesion, in particular, is necessary for clean removal of the transdermal patch.

A primary use of the adhesive may be to affix a patch to the skin. However, it is preferable for the drug to be delivered to be incorporated into the adhesive, where possible, in order to reduce the amount of components and, therefore, expense necessary to make the patch.

A number of adhesives are already available for se in transdermal patches. Acrylic polymers are commonly used, as these possess adhesive properties which may easily be modulated by changing the composition of the polymer.

In connection with transdermal patches, U.S. Pat. No. 5,413,776 discloses the use of a copolymer adhesive consisting of an acrylic acid ester polymer portion in combination with an N-vinyl-2 pyrrolidone polymeric portion. EP-A-450986 discloses the use of an alkyl methacrylate (co)polymer in combination with silicic acid anhydride, specifically for the delivery of nicotine. Both adhesives are acrylic copolymers.

EP-A-0450986 further discloses that a multi-functional monomer may be included as a copolymer, to provide chemical cross-links between the copolymer strands. Chemical cross-linking is thought to increase the degree of polymerisation and, thus, cohesion of the adhesive.

Block copolymers have also been used as adhesives for transdermal patches. A block copolymer consists of a mixture of 'hard' (A) and 'soft' (B) segments, which may be combined in an A-B-A or $(A-B)_n$ type structure (c.f. Block Copolymers: Overview and Critical Survey, Noshay and McGrath, 1977). Association of the hard segments is thought to provide a degree of physical cross-linking, which improves the cohesive properties of the adhesive. One such example of a block copolymer adhesive is a polystyrene-polyisoprene-polystyrene (SIS) which is an A-B-A type block copolymer adhesive made by Shell, for example. This adhesive requires the use of an additional tackifier to provide suitable tack to the adhesive.

U.S. Pat. No. 5,066,728 discloses a multiblock copolymer comprising endblocks of phenylbutadiene and an elastomeric midblock of a conjugated diene such as isoprene or butadiene. The copolymer is cross-linkable by electron beam radiation, such that the crosslinks are confined primarily to the end-block domains in the polymer, with minimal crosslinking occurring in the rubbery matrix. Blends of the copolymer with tackifier resins provide curable pressure sensitive adhesives.

JP-62036412A discloses vinyl chloride resins, produced by a graft copolymerisation of vinyl chloride and a block copolymer, wherein the copolymer contains a soft segment that is crosslinked. The resins reportedly have a excellent impact resistance, weather-proofing properties and bending elasticity.

WO-97/01589 also discloses graft copolymers, suitable for use in influencing optical quality, dyeabilty, stability to weather or impact cracking and stress cracking in moulding compositions. The graft copolymers comprise a soft segment with at least one acrylate monomer, and a hard segment comprising at least one vinyl aromatic monomer. The soft segment is cross-linked, and the hard and soft segments are overlaid.

While a number of adhesives are available for use in transdermal patches, there is still a need for transdermal patch adhesives which possess excellent tack, cohesion and improved drug storage capacity.

It has now, surprisingly, been found that a degree of chemical cross-linking between the soft segments of a block copolymer can cause the copolymer to have enhanced properties, particularly with regard to cohesion and drug storage properties.

Thus, in a first aspect, the present invention provides a cross-linked block copolymer having drug retention properties, the block copolymer having hard and soft segments, characterised in that there is cross-linking between the soft segments.

Preferably, the block copolymer is an acrylic block copolymer. It is also preferred that the block copolymer is capable of acting as an adhesive, preferably on its own, but also in conjunction with one or more substances, such as those typically used in the manufacture of transdermal patches.

Thus, in a preferred aspect, there is provided a block copolymer, preferably an acrylic block copolymer, comprising soft and hard segments, that is suitable for use as an adhesive, characterised in that there is a degree of chemical cross-linking between the soft segments.

It will be appreciated that the term 'drug', as used herein, refers to any substance or compound suitable for administration via a transdermal patch. A substance having drug retention properties is taken herein as being a substance capable of absorbing or adsorbing a drug. In the instance where the substance is loaded with drug for dispensing via a transdermal patch, then it will be appreciated that such absorbance and/or adsorbance should be at least partially reversible.

The block copolymers of the present invention are simple to manufacture in an economic fashion, and may be selected for their drug retention and/or adhesive/cohesive properties. Accordingly, it is possible to provide an adhesive for use with a transdermal patch which allows the delivery of a greater amount of drug than is currently possible using known adhesives, as well as providing cleaner removal of used patches.

The term 'block copolymer', as used herein, refers to a macromolecule comprised of two, or more, chemically dissimilar polymer structures, terminally connected together (Block Copolymers: Overview and Critical Survey, Noshay and McGrath, 1977). These dissimilar polymer structures, sections or segments, represent the 'blocks' of the block copolymer. The blocks may generally be arranged in an A-B structure, an A-B-A structure, or a multiblock-$(A-B)_n$-system, wherein A and B are the chemically distinct polymer segments of the block copolymer.

It is generally preferred that the block copolymer of the present invention is of an A-B-A structure, especially wherein one of A and B is an acrylic type polymeric unit. It will be appreciated that the present invention is also applicable to block copolymers which possess three, or more different 'blocks', such as an A-B-C block copolymer. However, for convenience, reference hereinafter to block copolymers will assume that there are only A and B sub-units, but it will be appreciated that such reference also encompasses block copolymers having more than two different sub-units, unless otherwise specified.

It will be appreciated that the properties of block copolymers are very largely determined by the nature of the A and B blocks. Block copolymers commonly possess both 'hard' and 'soft' segments. A 'hard' segment is a polymer that has a glass transition temperature $(T_g)$ and/or a melting temperature $(T_M)$ that is above room temperature, while a soft segment is a polymer that has a $T_g$ (and possibly a $T_M$) below room temperature. The different segments are thought to impart different properties to the block copolymer. Without being constrained by theory, it is thought that association of the hard segments of separate block copolymer units result in physical cross-links within the block copolymer, thereby promoting cohesive properties of the block copolymer. It is particularly preferred that the hard segments of the block copolymers of the present invention form such physical close associations.

The present invention preferably relates to acrylic block copolymers. In acrylic block copolymers, at least one of the blocks of the block copolymer is an acrylic acid polymer, or a polymer of an acrylic acid derivative. The polymer may be composed of just one repeated monomer species. However, it will be appreciated that a mixture of monomeric species may be used to form each of the blocks, so that a block may, in itself, be a copolymer. The use of a combination of different monomers can affect various properties of the resulting block copolymer. In particular, variation in the ratio or nature of the monomers used allows properties such as adhesion, tack and cohesion to be modulated, so that it is generally advantageous for the soft segments of the block copolymer to be composed of more than one monomer species.

It is preferred that alkyl acrylates and alkyl methacrylates are polymerised to form the soft portion of the block copolymer. Alkyl acrylates and alkyl methacrylates are thought to provide properties of tack and adhesion. Suitable alkyl acrylates and alkyl methacrylates include n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecyl acrylate and tridecyl methacrylate, although other suitable acrylates and methacrylates will be readily apparent to those skilled in the art. It is preferred that the acrylic block copolymer comprises at least 50% by weight of alkyl acrylate or alkyl methacrylate (co) polymer.

A polar monomer is advantageously copolymerised with the alkyl acrylate or alkyl methacrylate where it is desired to enhance the drug solubility of certain, especially hydrophilic, drugs. Suitable polar monomers which can be copolymerised with alkyl acrylates or alkyl methacrylates include hydroxyethyl acrylate, hydroxypropyl acrylate, vinyl pyrrolidone, acrylamide, dimethylacrylamide, acrylonitrile, diacetone acrylamide and vinyl acetate, although others will be apparent to those skilled in the art.

Diacetone acrylamide, or a combination of diacetone acrylamide and vinyl acetate, is useful in the present invention. The diacetone acrylamide component enables more advantageous drug loading capabilities than vinyl acetate, but vinyl acetate enhances the rate of polymerisation, which is of commercial importance. In such a case, where two polar monomers are used in an adhesive, it will be appreciated that the levels of each monomer may be manipulated in such a way as to provide optimum drug retention and delivery.

As stated above, variation in the components of the soft segment affects the overall properties of the block copolymer, although the essential feature remains the cross-linking of the soft segments. For example, soft segments consisting essentially of diacetone acrylamide with either butyl acrylate and/or 2-ethylhexyl acrylate, in approximately equal proportions, work well, and a ratio by weight of about 3:4:4 provides good results. It is preferred that diacetone acrylamide, or other polar monomer, such as hydroxyethyl methacrylate or vinyl acetate, be present in no more than 50% w/w of the monomeric mix of the soft segment, as this can lead to reduced adhesion, for example. However, where adhesion is not important, good levels of drug loading may be obtained with an excess of polar monomer. The acrylate component may generally be varied more freely, with good results observed with both 2-ethylhexyl acrylate and butyl acrylate together or individually, although with greater hydrophobic side chain size, there is a slight decrease in drug loading, both for hydrophobic and hydrophilic drugs.

As noted above, ratios of the various monomers are generally preferred to be approximately equal. For adhesives, this is preferred to be with a polar component of 50% or less of the soft segment, with the apolar portion forming up to about 85% w/w, but preferably between about 50 and 70% w/w. In the example above, this is about 72% (4+4) apolar to about 18% (3) polar.

In general, it is preferred that the combination of monomers chosen produces an adhesive, and that the adhesive has a combination of good drug loading, cohesion and adhesion, such that it is suitable for use with a transdermal patch. When varying the monomers and their different ratios, it is preferred to retain good drug loading properties.

Prior art adhesives are generally capable of drug loading of up to about 5% w/w adhesive. Block copolymers of the present invention, depending on composition, can often load in excess of 15%, but loading of between 5 and 10% is readily obtainable. Drug loading of less than 5% is occasionally observed, depending on the constitution and method of preparation of the block copolymer, but this is acceptable, especially where other properties, such as cohesion, are important.

It will be appreciated that compounds with high drug retention properties but reduced adhesion may also be suitable as an adhesive for use with a medical patch. Such adhesives may be appropriate for use in a transdermal patch which need only be applied for a short time or, alternatively, the adhesive may be used in combination with a further agent, such as an enhancer, for example polyethylene glycol, Azone™ (Laurocapram, or 1-Dodecylhexahydro-2H- azepine-2-one), vitamin E or liquid paraffin, to increase its adhesive properties.

As discussed above, polymers suitable for use as the hard portion of the block copolymer possess glass transition temperatures above room temperature. Suitable monomers for use in forming the hard segment polymer include styrene, α-methylstyrene, methyl methacrylate and vinyl pyrrolidone, although other suitable monomers will be readily apparent to those skilled in the art. Styrene and polymethyl methacrylate have been found to be suitable for use in the formation of the hard segment of the block copolymers of the present invention.

It is preferred that the hard portion of the block copolymer forms from 3–30% w/w of the total block copolymer, particularly preferably from 5–15% w/w.

The block copolymer of the present invention is one wherein the soft portions contain a degree of chemical cross-linking. Such cross-linking may be effected by any suitable cross-linking agent. It is particularly preferable that the cross-linking agent be in the form of a monomer suitable for incorporation into the soft segment during polymerisation. Preferably the cross-linking agent has two, or more, radically polymerisable groups, such as a vinyl group, per molecule of the monomer, at least one tending to remain unchanged during the initial polymerisation, thereby to permit cross-linking of the resulting block copolymer.

Suitable cross-linking agents for use in the present invention include divinylbenzene, methylene bis-acrylamide, ethylene glycol di(meth)acrylate, ethylene glycol tetra(meth)acrylate, propylene glycol di(meth)acrylate, butylene glycol di(meth)acrylate, or trimethylolpropane tri(meth)acrylate, although other suitable cross-linking agents will be readily apparent to those skilled in the art. A preferred cross-linking agent is tetraethylene glycol dimethacrylate. It is preferred that the cross-linking agent constitutes about 0.01–0.6% by weight of the block copolymer, with 0.1–0.4% by weight being particularly preferred.

Methods for the production of block copolymers from their monomeric constituents are well known. The block copolymer portions of the present invention may be produced by any suitable method, such as step growth, anionic, cationic and free radical methods (Block Copolymers, supra). Free radical methods are generally preferred over other methods, such as anionic polymerisation, as the solvent and the monomer do not have to be purified.

Suitable initiators for polymerisation include polymeric peroxides with more than one peroxide moiety per molecule. One suitable initiator has been found to be 'Perhexa MC' (1,1'-di-teributyl-peroxy-2-methyl cyclohexane, Nihon Yusi C.C.). This compound contains two tertiary butyl peroxy groups which allow stepwise polymerisation of the hard and soft segments of the block copolymer. The initiator CH-50-AL (Peroxid-Chemie GmbH) has also been found to be suitable in the manufacture of compounds of the present invention. Choice of reaction conditions is well within the skill of one in the art, once a suitable initiator has been chosen.

The initiator is preferably used in an amount of 0.005–0.1% by weight of the block copolymer, with 0.01–0.05% by weight being particularly preferred, although it will be appreciated that the amount chosen is, again, well within the skill of one in the art. In particular, it is preferred that the amount should not be so much as to cause instant gelling of the mix, nor so low as to slow down polymerisation and to leave excess residual monomers. A preferred level of residual monomers is below 2000 ppm. It will also be appreciated that the amount of initiator will vary substantially, depending on such considerations as the initiator itself and the nature of the monomers.

The block copolymers of the present invention are preferably adhesives, particularly preferably pressure sensitive adhesives. Pressure sensitive adhesives can be applied to a surface by hand pressure and require no activation by heat, water or solvent. As such, they are particularly suitable for use with transdermal patches. Block copolymer adhesives of the present invention are particularly suitable for use in combination with a transdermal patch.

A number of adhesives currently used in transdermal patches require the use of a tackifier, to provide improved tack. The block copolymers of the present invention are suitable for use without a tackifier and, as such; are particularly advantageous. However, it will be appreciated that the block copolymers of the present invention are also suitable for use in combination with a tackifier, should one be required or desired. Suitable tackifiers are well known and will be readily apparent to those skilled in the art.

Without being constrained by theory, it is thought that the combination of chemical cross-links between the soft segments of the copolymer combined with the, generally, hydrophobic interaction, or physical cross-linking, between the hard portions results in a 'matrix-like' structure. Copolymers having only physical cross-linking of the hard segments are less able to form such a matrix. It is believed that the combination of both forms of cross-linking of the block copolymers of the present invention provides both the increased internal strength (cohesion) and also the significantly improved drug storage capacity that is observed.

Essentially, it is believed that the hard segments associate to form islands, or nodes, with the soft segments radiating from and between these nodes. Where the soft segment is the B segment of an ABA structure, then it needs to be as long as possible to permit ingress of the drug.

In the block copolymers of the present invention, there is a defined physical structure in the 'sea' between the islands, where the soft segments are cross-linked, so that there is no necessity for extensive intermingling of the soft segments. This results in a greater cohesion of the whole block copolymer while, at the same time, allowing shortened soft segment length and still having as great, or greater, distances between the islands. This permits greater drug storage capacity. Even where soft segment length is reduced to 50% or lower than that of the art, the adhesives still have a greater cohesion and can also be manufactured more easily (infra).

It is thought that the ability of a copolymer adhesive to retain a drug is related to the length of the copolymer chains and the degree of cross-linking. The improved drug storage capacity of the block copolymer of the present invention allows reduction in the length of polymer chains in comparison to other copolymers that are used as adhesives, while still providing improved drug storage. Further, shortening of the polymer chains reduces the viscosity of the block copolymer, which is particularly advantageous in the manufacture of the adhesive.

Thus, there is further provided a transdermal patch comprising a block copolymer of the present invention, the block copolymer preferably being an adhesive.

The term 'transdermal patch', as used herein, is used to describe any means which may be applied to the skin and which may be used to deliver a drug or pharmaceutical preparation onto, and preferably through, the skin layer, typically the dermis. Transdermal patches generally comprisesa drug-impermeable backing portion and an adhesive.

The adhesive serves to stick the patch onto the skin and may also serve to contain and deliver the drug. The transdermal patch may be any patch that is suitable for use in combination with the block copolymer adhesive of the present invention.

It will be appreciated that the enhanced drug storage capacity of the block copolymer of the present invention allows improvements to be made in the design of transdermal patches. For example, patches which are smaller than those currently available can be made and which may still supply a therapeutically effective amount of a drug owing to the greater drug storage capacity and delivery of the block copolymers of the present invention.

The block copolymer of the present invention also allows for more straightforward manufacturing of transdermal patches. Acrylic adhesives which may be used in transdermal patches are commonly cross-linked to harden them by the use of isocyanates. However, isocyanate cross-linking must be carried out just prior to coating of a transdermal patch, because the cross-linking reaction begins immediately. If the adhesive is left to cross-link for too long, then it can no longer be coated onto the patch. However, the block copolymer of the present invention cross-links as the solvent is removed, so that cross-linking can be timed to occur after coating, this being the preferred method. Accordingly, not only can the block copolymer easily be applied to the patch, but the complete solution can also be stored for a period before coating.

Accordingly, there is also provided a process for the manufacture of a cross-linked block copolymer having drug retention properties, the block copolymer having hard and soft segments, there being cross-linking between the soft segments, the process comprising polymerising the monomeric constituents of each soft segment in solution, then adding the constituents of the hard segment to each resulting solution and polymerising the resulting mix, followed by cross-linking by removal of any solvent.

There is also provided such a complete solution, which provides cross-linked block copolymer of the present invention on removal of the solvent or solvent system, such as by evaporation. If the solution is to be stored for any length of time, it may be necessary to keep the polymer from precipitating out, and this may be achieved by known means, such as by suspending agents or shaking. It may also be necessary to select the type of polymers that will be subject to substantially no cross-linking until the solvent is evaporated.

Suitable examples of drug-impermeable backings which may be used for transdermal patches include films or sheets of polyolefins, polyesters, polyurethanes, polyvinyl alcohols, polyvinyl chlorides, polyvinylidene chloride, polyamides, ethylene-vinyl acetate copolymer (EVA), ethylene-ethylacrylate copolymer (EEA), vinyl acetate-vinyl chloride copolymer, cellulose acetate, ethyl cellulose, metal vapour deposited films or sheets thereof, rubber sheets or films, expanded synthetic resin sheets or films, non-woven fabrics, fabrics, knitted fabrics, paper and foils. Other backings will be readily apparent to those skilled in the art.

Suitable drugs are typically biologically active compounds or mixture of compounds that have a therapeutic, prophylactic or other beneficial pharmacological or physiological effect. Examples of drugs that may be used in combination with the block copolymer of the present invention include anti-arrhythmic drugs, anticoagulants, antidiabetics, antiepileptics, antifungals, antigout, antimalarials, antimuscarinic agents, antineoplastic agents, antiprotozoal agents, thyroid and antithyroid agents, anxiolytic sedatives and neuroleptics, beta blocking agents, drugs affecting bone metabolism, cardiac inotropic agents, chelating agents, antidotes and antagonists, corticosteroids, cough suppressants, expectorants and mucolytics, dermatological agents, diuretics, gastro-intestinal agents, general and local anaesthetics, histamine H1 receptor antagonists, nitrates, vitamins, opioid analgesics, parasympathomimetics, anti-asthma agents, muscle relaxants, stimulants and anorectics, sympathomimetics, thyroid agents, xanthines, lipid regulating agents, antiinflamatory drugs, analgesics, antiarthritic drugs, antispasmodics, antidepressants, antipsychotic drugs, tranquillisers, narcotic antagonists, antiparkinsonism agents, cholinergic agonists, anticancer drugs, immunosupressive agents, antiviral agents, antibiotic agents, appetite suppressants, antiemetics, anticholinergics, antihistamines, antimigraine agents, coronary, cerebral or peripheral vasodilators, hormonal agents, contraceptive agents, antithrombotic agents, diuretics, antihypertensive agents and cardiovascular drugs. Other drugs will be readily apparent to those skilled in the art.

Examples of specific drugs include steroids such as estradiol, levonorgestrel, norethisterone, testosterone and their esters; nitro-compounds such as nitroglycerine and isosorbide nitrates; nicotine, scopolamine; oxicam derivatives such as lornoxicam, ketoprofen, fentanyl, salbutamol, terbutaline, selegiline and clonidine, as well as pharmaceutically acceptable equivalents thereof and pharmaceutically acceptable esters and the salts of such compounds with pharmaceutically acceptable acids and bases as appropriate.

It will be appreciated that the above classes of drug, or specific drugs, are individually contemplated for use with a transdermal patch of the present invention.

It will be appreciated that, while various drugs have been exemplified above, some drugs are more suitable for use in transdermal delivery systems than others. While a transdermal delivery system may deliver a quantity of a drug, this quantity may not be the optimum therapeutic dose. Essentially, any drug that can be delivered by a patch and which does not substantially crystallise at levels too low to be useful is envisaged as being useful in patches of the present invention.

It will be appreciated that the present invention also envisages the use of permeation enhancers which allow greater permeation of the drug into the skin. Compounds suitable for use as permeation agents include compounds containing at least one amide bond, esters of lactic acid, lactic acid, salts of lactic acid, dicarboxylicacids, salts of dicarboxylic acids, citric acid and salts of citric acid, O-alkyl (polyoxyethyl)phosphates and esters of higher fatty acids, carboxylic acids of glycerin and ethers of polyoxyethylene and monoalcohols. Suitable enhancers include lauryl di-methanol amide, glycerin monolaurate, glycerin triacetate and polyoxyethylene lauryl ether.

Other specific examples of permeation enhancers include PEG (polyethylene glycol), liquid paraffin, Azone and vitamin E. In addition, such enhancers may improve the adhesive qualities of the block copolymer of the invention and, where used, it may be desirable to select an adhesive with lower adhesive properties. Alternatively, such enhancers may be used to supplement a block copolymer having low adhesive qualities.

The present invention also envisages the use of suitable agents to inhibit crystallisation of the drug in the adhesive. Many agents will be apparent to those skilled in the art, and polyethylene glycol is generally particularly effective.

However, it has been found that a further advantage of the adhesives of the present invention is that compounds to be delivered are generally less likely to crystallise than they are in prior art systems.

The present invention will now be illustrated further with reference to the following, non-binding Examples.

EXAMPLE 1

Drug Saturation

The ability of the block copolymer of the present invention to store drugs was compared with a polystyrene-polyisoprene-polystyrene based adhesive (hereinafter termed 'SIS') used in transdermal patches (KrantonD-1101™, Shell Chemicals).

For the purpose of the comparative studies, the SIS block copolymer was mixed with tackifier (Arkon P-100, Arakawa Chemicals, Osaka, Japan) and paraffin in the ratio 1:1.6:1.2 by weight respectively. This mixture provides optimised adhesive properties.

Three drugs, isosorbide mononitrate (ISMN), indomethacin and ketoprofen, were used in the present Example. Each of the drugs was mixed with each of the two adhesives, such that a range of concentrations of drug were obtained in each adhesive. Each adhesive/drug mix was then applied to a backing film, and the film allowed to dry. After drying, the films were assessed for drug crystallisation.

More specifically, the compound of the present invention was dissolved in ethyl acetate to form 39% by weight of the final solution. The SIS adhesive was dissolved in chloroform, to a final concentration of 19% by weight of the final solution. Each drug was dissolved in methanol to a final concentration of 5% by weight.

The adhesives and drug solutions were mixed together in suitable proportions such that a range of different drug concentrations were produced. The mix was then applied to a polyethylene terephthalate (herein abbreviated to 'PET') film. The solvents were evaporated off at 60° C., such that thin films of adhesive containing the drug were left. All the films were then left at 50° C. for 48 hours, then room temperature for 48 hours. Crystal formation was assessed.

The following range of drug concentrations was chosen:

SIS adhesive: 1%, 2%, 3%, 5%, 7.5%, 10% (w/w adhesive)

Adhesive of the invention: 10%, 12.5%, 15%, 17.5%, 20% (w/w adhesive)

It was not possible to obtain concentrations of drug above 10% in the SIS adhesive. The saturation concentration of each drug was determined, which was defined as the maximum concentration of drug at which no crystal formation was observed. The results of the experiment are shown in Table 1 below.

TABLE 1

| | Saturation concentration (% w/w adhesive) | |
|---|---|---|
| Drug | Adhesive of the invention | SIS |
| ISMN | >20% | 5% |
| Ketoprofen | 17.5% | 1 |
| Indomethacin | 15 | <1% |

It can be seen from the above Table that drug crystallised in the SIS adhesive at very substantially lower concentrations than in the compound of the invention, both ketoprofen and indomethacin being essentially unusable in SIS. Thus, the compound of the present invention is able to incorporate greater quantities of drug than SIS adhesive before crystal formation occurs.

EXAMPLE 2

Drug Delivery

The ability of an adhesive compound of the present invention to release ISMN was compared to that of the SIS adhesive.

Transdermal patches were manufactured, each containing each of the adhesives in combination with ISMN. The test patches were applied to two volunteers for 24 hours. After this time, the test patches were removed, and the residual drug levels were measured. The quantity of ISMN in a standard (control) patch was measured, to obtain a reference value. Comparison of the residual drug content of the test patches with the total drug content of the control patch allows the total amount of drug release from the patch to be determined.

More specifically, a 20% w/w solution of ISMN in methanol was prepared. The ISMN solution was mixed with a quantity of either the SIS adhesive or the adhesive of the present invention, sufficient to obtain the desired final drug concentration. Each adhesive-drug mix was coated onto a 30 $\mu$m PET film (release liner). Thus, after drying, the adhesive layer had been laminated onto a PET backing film. The films were then punched to form circular patches of 3cm diameter.

After having been used on the patients for 24 hours, patches containing the SIS adhesive were placed in 15 cm$^3$ of chloroform for 24 hours to dissolve the ISMN. Methanol was then used to precipitate the ISMN from the chloroform solution. ISMN levels were then determined by High Pressure Liquid Chromatography (HPLC).

Patches containing the adhesive of the present invention were placed directly in 30cm$^3$ of methanol for 24 hours, in order to dissolve the remaining ISMN. The concentration of ISMN was determined by HPLC as above.

In this latter case, methanol alone is sufficient to release drug from the adhesive of the present invention, and a chloroform step is not required. For comparative purposes, it has been shown that a chloroform-methanol extraction of ISMN from the adhesive of the present invention produces identical results to that of a simple methanol extraction. Thus, the results below are directly comparable and are not affected by the different extraction techniques used.

Drug release from the following patches was assessed, and the results are shown in Table 2 below.

TABLE 2

| Adhesive | ISMN Concentration (% w/w of the adhesive) |
|---|---|
| Adhesive of present invention | 10% and 20% |
| SIS adhesive | 3% and 5% |

It was not possible to provide more than 5% w/w of ISMN in the SIS adhesive. Therefore, the relative drug release from the different adhesives is not directly comparable. However, it is the absolute amount of drug release that is important in this case. Table 3 below shows the effective maximum levels of drug release to the volunteer for each adhesive.

TABLE 3

|  | Adhesive | | | |
| --- | --- | --- | --- | --- |
|  | Adhesive of the present invention (10% ISMN) | Adhesive of the present invention (20% ISMN) | SIS (3% ISMN) | SIS (5% ISMN) |
| Drug content (mg) | | | | |
| Control patch | 6.5 | 9.8 | 1.9 | 3.83 |
| Residual drug content (mg) | | | | |
| Volunteer A | 4.6 | 7.4 | 1.54 | 2.38 |
| Volunteer B | 5.1 | 8.1 | 1.88 | 3.48 |
| Total drug release (mg) | | | | |
| Volunteer A | 1.9 | 2.4 | 0.46 | 1.45 |
| Volunteer B | 1.4 | 1.7 | 0.02 | 0.35 |

From the above table, it can be seen that the total drug that may be released from the patch is much greater when the adhesive of the present invention is used. This is related to the ability of the adhesive of the present invention to contain a greater initial quantity of drug. Further, drug release continues from the patches of the invention after the test period of 24 hours.

EXAMPLE 3

Preparation of Adhesive Compounds of the Present Invention

The adhesive compound used in Examples 1 and 2 was made in a two step synthesis.

Step 1:

115 g of 2-ethylhexyl acrylate, 84 g of diacetone acrylamide, 115 g of butyl acrylate and 0.72 g tetraethylene glycol dimethacrylate were mixed, in order to obtain a homogeneous solution. The solution was placed in a flask, and 200 cm$^3$ of ethyl acetate along with 200 cm$^3$ of toluene were added. The solution was heated to 80° C. under nitrogen, then 0.05 g of 1,1'-di-teri-butylperoxy-2-methyl cyclohexane dissolved in 10 cm$^3$ of ethyl acetate were added. Polymerisation was allowed to proceed for 24 hours. This step produced the soft segments.

Step 2:

After 24 hours, 45 g methyl methacrylate and 300 cm$^3$ of toluene were added to the mix of Step 1. The solution was then heated to 99° C. in order to initiate the second stage polymerisation step, which was continued for 12 hours.

After this time, the polymer was transferred to a bottle for cooling. The resulting solution represented a pre-crosslinked polymer, used in subsequent experiments. The average molecular weight of the polymer produced in this way was estimated to be 358,000 Da by gel permeation chromatography.

EXAMPLE 4

Comparative Cohesion Studies

There are no industry standard tests for measuring cohesion. Cohesive strength of the adhesives was assayed as follows.

The polymer solution of Example 3 was applied to a backing strip. Evaporation of the solvent resulted in a cross-linked adhesive compound. One end of the strip was then stuck to a glass plate, angled at 20° from the vertical. The rest of the strip was allowed to hang vertically. A weight was then suspended from the free end of the strip. The time taken for the strip to detach from the plate (i.e. for the strip and weight to fall to the ground) was measured.

More specifically, in this Example, the SIS adhesive was compared with the adhesive compound of the present invention. The SIS adhesive contained 5%, by weight, of ISMN, while the adhesive of the present invention contained 10% by weight of ISMN.

Strips of length 5 cm and width 0.6 cm, coated with one of each of the adhesive-drug mixtures, were attached to a glass plate. The total adhesion area in each case was 0.36 cm$^2$. An 80 g weight was used. The measurements were taken at 25° C.

The time taken for each strip to become detached from the plate is shown in Table 4 below.

TABLE 4

|  | Time taken to become detached | |
| --- | --- | --- |
|  | Adhesive of the invention | SIS adhesive |
| Sample Strip 1 | >30 minutes* | 7.5 minutes |
| Sample Strip 2 | >30 minutes* | 6.0 minutes |

*Detached by 24 hours

It can be seen from the above table that the adhesive of the present invention takes significantly longer to become detached from the glass plate, in comparison with the SIS adhesive under the same conditions. Therefore, the adhesive of the present invention has significantly enhanced cohesive properties with respect to the SIS adhesive.

EXAMPLE 5

Effects of Variation in Monomer Composition

A number of variations of the adhesive of the invention were prepared, in order to determine the effect of variation in the composition.

5.1 Initial variants were tested for cohesion. The compositions tested are shown in Table 5 below.

TABLE 5

| | Composition | | | | | | | |
| --- | --- | --- | --- | --- | --- | --- | --- | --- |
| Component | A | B | C | D | E | F | X | Y |
| 2-ethylhexyl acrylate (g) | 115 | 115 | 115 | 115 | 115 | 115 | 258 | 258 |
| Butyl acrylate (g) | 115 | 115 | 115 | 115 | 115 | 115 | | |
| Diacetone acrylamide (g) | 84 | 84 | 84 | 84 | 84 | 21 | 42 | 42 |
| Ethyl acrylate (g) | | | | | | 63 | | |

TABLE 5-continued

| | Composition | | | | | | | |
|---|---|---|---|---|---|---|---|---|
| Component | A | B | C | D | E | F | X | Y |
| Tetraethylene glycol dimethacrylate (g) | 0.72 | 0.72 | 0.36 | 0.48 | 1.5 | 0.48 | 0.24 | 0.48 |
| Methyl methacrylate (g) | 45 | 30 | 45 | 30 | 45 | 30 | 30 | 30 |
| Cohesion (min's) | >20 | 3–10 | 3–10 | <3 | N/A[1] | N/A[1] | <1 | <1 |

[1]Data not available

In all the above cases, the solvents used were toluene (500 mls) and ethyl acetate (200 mls). The initiator was Perhexa MC (0.05 mg) in all cases.

From the above, it can be seen that composition A represents an adhesive with excellent cohesion. The results obtained with B and C indicate some of the variations that can be made and a suitable composition still obtained.

Composition D contains comparatively low levels of both tetraethylene glycol dimethacrylate and methyl methacrylate. This adhesive has lowered cohesion compared with B or C, each of which have only of these two amounts reduced.

Compositions E and F produce gel-like polymers, which are not preferred as an adhesive suitable for use with a transdermal patch, while X and Y had low levels of each of diacetone acrylamide, tetraethylene glycol dimethacrylate and methyl methacrylate, and produced a sticky polymer with weak cohesion.

5.2 A number of further adhesives were made, with different compositions. These were tested for adhesion, cohesion and drug retention. These compositions and properties are presented in Table 6 below.

From the above, it can be seen that compositions G, H, I, K, L, M and N show good drug retention properties, in combination with suitable cohesive and adhesive properties. These adhesives are suitable for use in combination with transdermal patches.

Compounds J and O, which have high levels of tetraethylene glycol dimethacrylate and Perhexa MC, produced a product which gelled at the first stage of polymerisation. Such compounds are not suitable for use as adhesives for transdermal patches.

Compound P, with a high level of hydrophilic monomers, produced a product with no adhesion. This compound is unsuitable for use as an adhesive for transdermal patches, unless adhesion can be generated in the presence of an enhancer. In any event, this compound may be suitable for use with transdermal patches as a drug retention agent, even if an extra adhesive is necessary, owing to its great drug retention.

COMPARATIVE EXAMPLE 1

Cohesion and Drug Loading Capacity of Commercially Available Adhesives

Two commercially available adhesives used in transdermal patches were tested for drug loading capacity, using the

TABLE 6

| | Composition | | | | | | | | | |
|---|---|---|---|---|---|---|---|---|---|---|
| | G | H | I | J | K | L | M | N | O | P |
| Monomer[1] | | | | | | | | | | |
| 2-Ethylhexyl acrylate | 110 | 110 | | | 55 | 55 | | 55 | 55 | |
| Butyl acrylate | | | 110 | 110 | 55 | 55 | 110 | 55 | 55 | 110 |
| Hydroxyethyl methacrylate | | | | | 75 | | | | | |
| Diacetone acrylamide | 110 | 55 | 75 | 75 | | 75 | | 75 | 75 | 100 |
| Vinyl acetate | | | | | | | 75 | 37.5 | 37.5 | 40 |
| Tetraethylene glycol dimethacrylate | 0.35 | 0.35 | 0.35 | 0.5 | 0.35 | 0.35 | 0.35 | 0.35 | 0.35 | 0.35 |
| Methyl methacrylate | 25 | 15 | 15 | 15 | 15 | — | 15 | 15 | 15 | 15 |
| Styrene | | | | | | 15 | | | | |
| Initiator[1] | | | | | | | | | | |
| Perhexa MC | 0.09 | 0.14 | 0.14 | 0.14 | 0.14 | 0.14 | 0.14 | 0.14 | 0.21 | 0.14 |
| Solvent[2] | | | | | | | | | | |
| Ethyl acetate | 200 | 200 | 200 | 200 | 200 | 200 | 200 | 300 | 300 | 300 |
| Toluene | 250 | 250 | 250 | 250 | 250 | 250 | 250 | 350 | 350 | 350 |
| Adhesive properties[3] | | | | | | | | | | |
| Adhesion | Slight | Good | Good | N/A[5] | Slight | Good | Slight | Good | N/A[5] | No adhesion |
| Cohesion | 5 | 10 | >15 | N/A[5] | 10 | >15 | 10 | >15 | N/A[5] | 0 |
| Drug loading property[4] | | | | | | | | | | |
| Piroxicam | 5 | 5 | 8 | N/A[5] | 5 | 6 | 4 | 8 | N/A[5] | 10 |
| Oestradiol | 8 | 8 | 15 | N/A[5] | 6 | 10 | <4 | 15 | N/A[5] | >15 |

[1]units = grams
[2]units = ml
[3]units = minutes
[4]units = grams per 100 g of adhesive
[5]Not available drugs piroxicam and estradiol. The adhesives were National Starch 837-2516 and National Starch 387-2052.

Each drug showed cohesion of greater than 15 minutes.

National Starch 837-2516 was able to hold 4 g of piroxicam and 4 g of estradiol, per 100 g of adhesive.

National Starch 837-2052 was able to hold 4 g of piroxicam and 2 g of estradiol, per 100 g of adhesive.

Thus, by comparison with Table 6 above, the National Starch adhesives show equivalent drug loading properties to composition M, while all other compounds of Table 6 for which drug loading was tested showed improved drug loading with respect to the commercially available products.

EXAMPLE 6

Use of Initiator CH-50-AL

Experiments were carried out using the initiator CH-50-AL, in place of Perhexa MC. CH-50-AL is 1,1-di(tert-butylperoxy)cyclohexane, and is available from Peroxid-Chemie GmbH. The compositions listed in Table 7 below were tested.

TABLE 7

|  | Composition | |
| --- | --- | --- |
|  | Q | R |
| Monomer[1] | | |
| 2-Ethylhexyl acrylate | 85 | 85 |
| Butyl acrylate | 85 | 85 |
| Diacetone acrylamide | 63 | 63 |
| Terraethylene glycol dimethacrylate | 0.25 | 0.25 |
| Methyl methacrylate | 20 | 20 |
| Initiator[1] | | |
| CH-50-AL | 0.1 | 0.1 |
| Solvent[2] | | |
| First stage | | |
| Ethyl acetate | 150 | 150 |
| Toluene | 150 | 50 |
| Second stage | | |
| Toluene | 150 | 150 |
| Temperature | | |
| first stage | 90 | 90 |
| second stage | 98 | 98 |
| Cohesive properties | | |
| Cohesion | 5 minutes | >20 minutes |

[1]units = grams
[2]units = mls.

What is claimed is:

1. An acrylic cross-linked block copolymer having hard and soft segments,
   wherein there is cross-linking between the soft segments, and the block copolymer has sufficient drug retention properties so that, when in a composition containing an amount of adhesive and ISMN, the composition has a saturation concentration of ISMN that is at least 10 percent on a weight to weight basis relative to the amount of adhesive in the composition.

2. The block copolymer of claim 1, wherein the block copolymer is an adhesive.

3. The block copolymer of claim 1, wherein the block copolymer is an adhesive when in conjunction with one or more adhesive enhancers.

4. The block copolymer of claim 1, which has an A-B-A structure.

5. The block copolymer of claim 1, which has as A-B-A structure and wherein one of A and B is an acrylic polymeric unit.

6. The block copolymer of claim 1, wherein the soft portion of the block copolymer comprises monomeric units selected from the group consisting of alkyl acrylates and alkyl methacrylates.

7. The block copolymer of claim 1, wherein said soft portion of said block copolymer comprises monomeric units selected from the group consisting of alkyl acrylates and alkyl methacrylates, and wherein said monomeric units are selected from the group consisting of n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecyl acrylate and tridecyl methacrylate and mixtures thereof.

8. The block copolymer of claim 1, wherein the block copolymer comprises an acrylic block copolymer, and the acrylic block copolymer comprises at least 50% by weight of alkyl acrylate or alkyl methacrylate (co)polymer.

9. The block copolymer of claim 1, wherein a polar monomer is copolymerised with the alkyl acrylate or alkyl methacrylate.

10. The block copolymer of claim 6, wherein a polar monomer is copolymerised with said alkyl acrylate or alkly methacrylate and said polar monomer is selected from hydroxyethyl acrylate, hydroxypropyl acrylate, vinyl pyrrolidone, acryl amide, dimethylacrylamide, acrylonitrile, diacetone acrylamide, vinyl acetate and mixtures thereof.

11. The block copolymer of claim 1, wherein the block copolymer comprises an adhesive that contains an agent to enhance adhesive properties of the block copolymer.

12. The block copolymer of claim 1, wherein the block copolymer comprises an adhesive containing an agent selected from the group consisting of polyethylene glycol, laurocapramii, vitamin E and liquid paraffin.

13. The block copolymer of claim 1, which is an adhesive, wherein said adhesive properties are enhanced by a further agent selected from lauryl di-methanol amide, glycerin monolaurate, glycerin triacetate or polyoxyethylene lauryl ether.

14. The block copolymer of claim 1, wherein said hard segment polymer is formed from a substance selected from the group consisting of styrene, α-methylstyrene, methyl methacrylate, vinyl pyrrolidone and mixtures thereof.

15. The block copolymer of claim 1, wherein said hard segment polymer is formed from a substance selected from the group consisting of styrene and polymethyl methacyrylate and mixtures thereof.

16. The block copolymer of claim 1, wherein the hard portion of the block copolymer forms from 3–30% w/w of the total block copolymer.

17. The block copolymer of claim 1, wherein the hard portion of the block copolymer forms from 5–15% w/w of the total block copolymer.

18. The block copolymer of claim 1, which is a pressure sensitive adhesive.

19. A transdermal patch comprising the block copolymer of claim 1.

20. A transdermal patch comprising the block copolymer of claim 1 which is loaded with a drug selected from the group consisting of, anti-arrhythic drugs, anticoagulants, antidiabetics, antiepileptics, antifungals, antigout, antimalarials, antimuscarinic agents, antieoplastic agents, antiprotozoal agents, thyroid and antithyroid agents, anxiolytic sedatives and neuroleptics, beta blocking agents, drugs affecting bone metabolism, cardiac inotropic agents, chelating agents antidotes and antagonists, corticosteroids, cough suppressants, expectorants and mucolytics, dermatological agents, diuretics, gastro-intestinal agents, general and local anesthetics, histamine H1 receptor antagonists, nitrates, vitamins, opioid analgesics, parasympathomimetics, anti-asthma agents, muscle relaxants, stimulants and anorectics, sympathomimetics, thyroid agents, xanthines, lipid regulating agents, anti-inflammatory drugs, analgesics, antiarthritic drugs, antispasmodics, antidepressants, antipsychotic drugs, tranquilizers, narcotic antagonists, antiparkinsonism agents, cholinergic agonists, anticancer drugs, immunosuppressive agents, antiviral agents, antibiotic agents, appetite suppressants, antiemetics, anticholinergics, antihistamines, antimigraine agents, coronary, cerebral or peripheral vasodilators, hormonal agents, contraceptive agents, anti-thrombotic agents, diuretics, antihypertensive agents and cardiovascular agents.

21. The patch of claim 20, wherein the drug is selected from the group consisting of steroids plus salts and esters thereof.

22. The patch of claim 20, wherein the drug is selected from the group consisting of estradiol, levonorgestrel, norethisterone, testosterone and salts and esters thereof.

23. The patch of claim 20, wherein the drug is selected from the group consisting of nitro-compounds plus salts and esters thereof.

24. The patch of claim 20, wherein the drug is selected from the group consisting of nitroglycerine, isosorbide nitrates and the salts and esters thereof.

25. The patch of claim 20, wherein the drug is selected from the group consisting of nicotine and scopolamine and salts and esters thereof.

26. The patch of claim 20, wherein the drug is selected from the group consisting of oxicam derivatives plus salts and esters thereof.

27. The patch of claim 20, wherein the drug is selected from the group consisting of lornoxicam, ketoprfen, fentanyl, salbutamol, tebutaline, selegiline and cloidine and salts and esters thereof.

28. A process for the manufacture of a cross-linked block copolymer having hard and soft segments, there being cross-linking between the soft segments, the process comprising polymerising the monomeric constituents of each soft segment in solution, said constituents including at least one cross-linking agent, then adding the constituents of the hard segment to each resulting solution and polymerising the resulting mix, followed by cross-linking by removal of any solvent, an initiator being added before adding the constituents of the hard segment, wherein the block copolymer has sufficient drug retention properties so that, when in a composition containing an amount of adhesive and ISMN, the composition has a saturation concentration of ISMN that is at least 10 percent on a weight to weight basis relative to the amount of adhesive in the composition.

29. The process of claim 28, wherein the block copolymer is so produced as to have the properties of a block copolymer of claim 1.

30. The process of claim 28, wherein the cross-linking agent is in the form of at least one monomer suitable for incorporation into the soft segment during polymerization.

31. The process of claim 30, wherein the at least one cross-linking agent has two, or more, radically polymerizable groups.

32. The process of claim 30, wherein the at least one cross-linking agent is selected from the group consisting of divinyl-benzene, methylene bis-acrylamide, ethylene glycol di(meth)acrylate, ethylene glycol tetra(meth)acrylate, propylene glycol di(meth)acrylate, butylene glycol di(meth)acrylate, and trimethylolpropane tri(meth)acrylate.

33. The process of claim 30, wherein the at least one cross-linking agent is tetraethylene glycol dimethacrylate.

34. The process of claim 30, wherein the cross-linking agent constitutes 0.01–0.6% by weight of the block copolymer.

35. The process of claim 30, wherein the cross-linking agent constitutes 0.1–0.4% by weight of the block copolymer.

36. The process of claim 28, wherein the initiator is 1,1'-di-tert-butylperoxy-2-methylcyclohexane.

37. The process of claim 28, wherein the initiator used is in an amount of 0.005–0.1% by weight of the block copolymer.

38. The process of claim 28, wherein the initiator is used in an amount of 0.01–0.05% by weight.

39. The process of claim 28, wherein a polar monomer comprises up to 50% w/w of the monomers of any soft segment.

40. The process of claim 39, wherein a polar monomer comprises in excess of 15% w/w of the monomers of any soft segment.

41. A transdermal patch comprising the block copolymer of claim 18.

42. A cross-linked block copolymer having hard and soft segments, wherein there is cross-linking between said soft segments, said soft segments comprise monomeric units selected from the group consisting of alkyl acrylates and alkyl niethacrylates, and said hard segment polymer comprises at least one monomer selected from the group consisting of styrene, a□methylstyrene, methyl methacrylate, vinyl pyrrolidone and mixtures thereof, and wherein the block copolymer has sufficient drug retention properties so that, when in a composition containing an amount of adhesive and ISMN, the composition has a saturation concentration of ISMN that is at least 10 percent on a weight to weight basis relative to the amount of adhesive in the composition.

43. The block copolymer of claim 42, wherein said hard segment portion of said block copolymer forms from about 3 to 30% w/w of total block copolymer.

44. The block copolymer of claim 42, wherein said soft segments further comprise at least one cross-linking agent in monomeric form, said cross-linking agent comprises a monomeric residue of a monomer having at least two radically polymerizable groups, and said soft segments are cross-linked via said cross-linking agent.

45. A cross-linked block copolymer having hard and soft segments, wherein there is cross-linking between said soft segments, said soft segment portion comprises monomeric units selected from the group consisting of alkyl acrylates and alkyl methacrylates, and diacetone acrylamide is an ingredient of at least one soft segment and wherein the block copolymer has sufficient drug retention properties so that, when in a composition containing an amount of adhesive and ISMN, the composition has a saturation concentration of ISMN that is at least 10 percent on a weight to weight basis relative to the amount of adhesive in the composition.

46. The block copolymer of claim 45, wherein said soft segments further comprise at least one cross-linking agent in monomeric form, said cross-linking agent comprises a monomeric residue of a monomer having at least two radically polymerizable groups, and said soft segments are cross-linked via said cross-linking agent.

47. A transdermal patch comprising the block copolymer of claim 42.

48. A transdermal patch comprising the block copolymer of claim 42.

49. An acrylic cross-linked block copolymer having hard and soft segments, wherein there is cross-linking between the soft segments, and the block copolymer has sufficient drug retention properties so that, when in a composition containing an amount of adhesive and ketoprofen, the composition has a saturation concentration of ketoprofen that is at least 10 percent on a weight to weight basis relative to the amount of adhesive in the composition.

50. The block copolymer of claim 49, wherein the block copolymer is an adhesive.

51. The block copolymer of claim 49, wherein the block copolymer is an adhesive when in conjunction with one or more adhesive enhancers.

52. The block copolymer of claim 49, which has an A-B-A structure.

53. The block copolymer of claim 49, which has as A-B-A structure and wherein one of A and B is an acrylic polymeric unit.

54. An acrylic cross-linked block copolymer having hard and soft segments, wherein there is cross-linking between the soft segments, and the block copolymer has sufficient drug retention properties so that, when in a composition containing an amount of adhesive and indomethacin, the composition has a saturation concentration of indometlhacini that is at least 10 percent on a weight to weight basis relative to the amount of adhesive in the composition.

55. The block copolymer of claim 54, wherein the block copolymer is an adhesive.

56. The block copolymer of clain 54, wherein the block copolymer is an adhesive when in conjunction with one or more adhesive enhancers.

57. The block copolymer of claim 54, which has an A-B-A structure.

58. The block copolymer of claim 54, which has as A-B-A structure and wherein one of A and B is an acrylic polymeric unit.

59. A process for the manufacture of a cross-linked block copolymer having hard and soft segments, there being cross-linking between the soft segments, the process comprising polymerising the monomeric constituents of each soft segment in solution, said constituents including at least one cross-linking agent, then adding the constituents of the hard segment to each resulting solution and polymerising the resulting mix, followed by cross-linking by removal of any solvent, an initiator being added before adding the constituents of the hard segment, wherein the block copolymer has sufficient drug retention properties so that, when in a composition containing an amount of adhesive and ketoprofen, the composition has a saturation concentration of ketoprofen that is at least 10 percent on a weight to weight basis relative to the amount of adhesive in the composition.

60. The block copolymer of claim 59, wherein the block copolymer is an adhesive.

61. The block copolymer of claim 59, wherein the block copolymer is an adhesive when in conjunction with one or more adhesive enhancers.

62. The block copolymer of claim 59, which has an A-B-A structure.

63. The block copolymer of claim 59, which has as A-B-A structure and wherein one of A and B is an acrylic polymeric unit.

64. A process for the manufacture of a cross-linked block copolymer having hard and soft segments, there being cross-linking between the soft segments, the process comprising polymerising the monomeric constituents of each soft segment in solution, said constituents including at least one cross-linking agent, then adding the constituents of the hard segment to each resulting solution and polymerising the resulting mix, followed by cross-linking by removal of any solvent, an initiator being added before adding the constituents of the hard segment, wherein the block copolymer has sufficient drug retention properties so that, when in a composition containing an amount of adhesive and indomethacin, the composition has a saturation concentration of indomethacin that is at least 10 percent on a weight to weight basis relative to the amount of adhesive in the composition.

65. The block copolymer of claim 64, wherein the block copolymer is an adhesive.

66. The block copolymner of claim 64, wherein the block copolymer is an adhesive when in conjunction with one or more adhesive enhancers.

67. The block copolymer of claim 64, which has an A-B-A structure.

68. The block copolymer of claim 64, which has as A-B-A structure and wherein one of A and B is an acrylic polymeric unit.

* * * * *